United States Patent
Acker et al.

(10) Patent No.: US 7,918,226 B2
(45) Date of Patent: Apr. 5, 2011

(54) METHOD AND SYSTEM FOR DETECTING BREATHING TUBE OCCLUSION

(75) Inventors: Jaron M. Acker, Madison, WI (US); Andrew P. Levi, Madison, WI (US); Andreas Tzanetakis, Helsinki (FI)

(73) Assignee: General Electric Company, Schenectady, NY (US)

( * ) Notice: Subject to any disclaimer, the term of this patent is extended or adjusted under 35 U.S.C. 154(b) by 908 days.

(21) Appl. No.: 11/733,438

(22) Filed: Apr. 10, 2007

(65) Prior Publication Data

US 2008/0255467 A1    Oct. 16, 2008

(51) Int. Cl.
*A61M 11/00* (2006.01)

(52) U.S. Cl. ............... 128/207.15; 128/204.21

(58) Field of Classification Search ............ 128/200.24, 128/200.18, 204.22, 204.23, 207.14, 207.15, 128/204.21
See application file for complete search history.

(56) References Cited

U.S. PATENT DOCUMENTS

| | | | |
|---|---|---|---|
| 5,423,313 A * | 6/1995 | Olsson et al. | 128/204.21 |
| 5,906,204 A * | 5/1999 | Beran et al. | 128/207.14 |
| 6,315,739 B1 * | 11/2001 | Merilainen et al. | 600/587 |
| 6,450,164 B1 * | 9/2002 | Banner et al. | 128/204.21 |
| 6,622,726 B1 | 9/2003 | Du | |
| 7,191,780 B2 | 3/2007 | Faram | |
| 7,320,320 B2 | 1/2008 | Berthon-Jones | |
| 2009/0266360 A1 | 10/2009 | Acker et al. | |

FOREIGN PATENT DOCUMENTS

| | | |
|---|---|---|
| EP | 0425092 A1 | 5/1991 |
| WO | 98/41268 A1 | 9/1998 |
| WO | 98/41269 A1 | 9/1998 |
| WO | 2006/034549 A2 | 4/2006 |

OTHER PUBLICATIONS

Maryam Zamanian, MD; John J. Marini, MD, "Pressure-flow signatures of central-airway mucus plugging," Crit Care Med. 2006, p. 223-226. vol. 34, No. 1.
Translation of First Examination Report in Swedish Patent Application No. 0950264-2 dated Nov. 20, 2009.
Translation of Second Examination Report in Swedish Patent Application No. 0950264-2 dated Sep. 15, 2010.

* cited by examiner

*Primary Examiner* — Steven O Douglas
(74) *Attorney, Agent, or Firm* — Andrus, Sceales, Starke & Sawall, LLP

(57) ABSTRACT

A method for identifying an occlusion in a breathing tube of a ventilator system is disclosed herein. The method includes obtaining data related to a respiratory signal, transferring the data to a processor, and implementing the processor to evaluate the data in a manner adapted to automatically identify the presence of an occlusion in the breathing tube. A corresponding ventilator system is also disclosed.

14 Claims, 2 Drawing Sheets

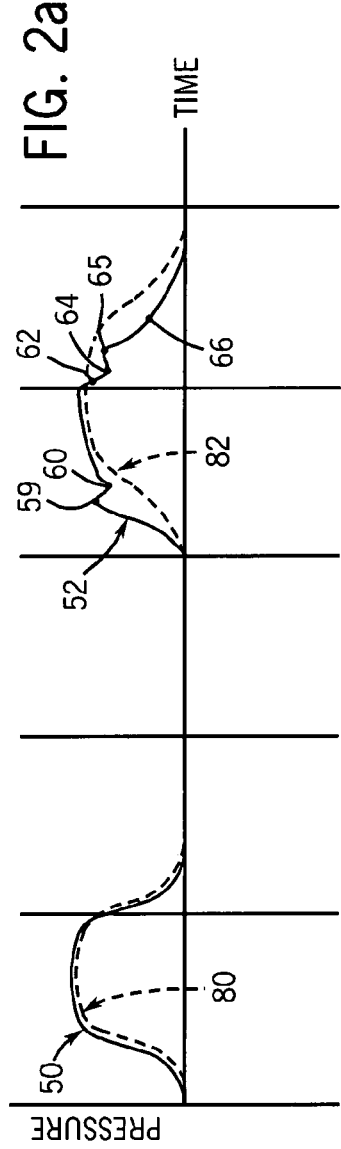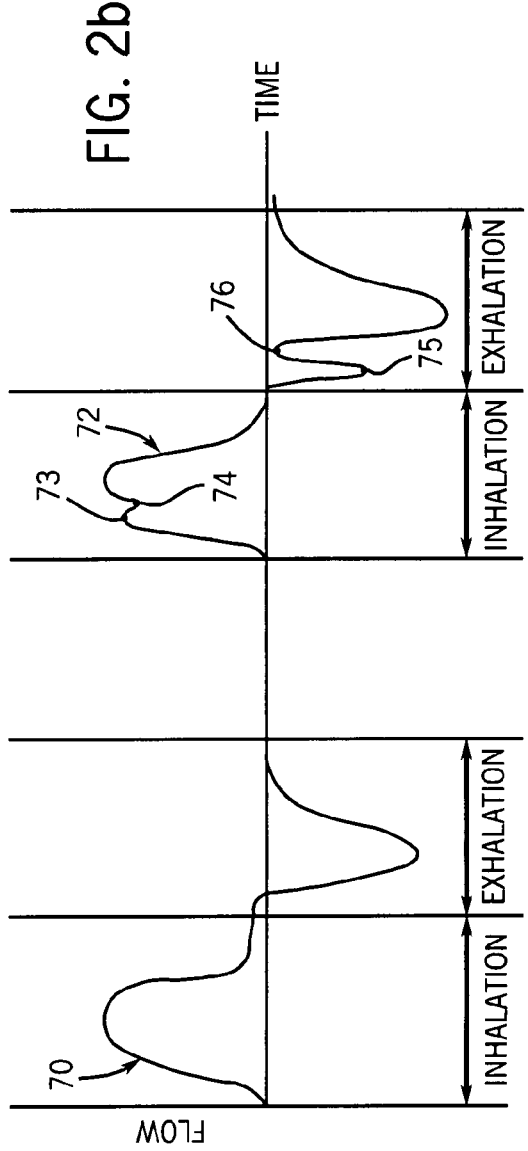

METHOD AND SYSTEM FOR DETECTING BREATHING TUBE OCCLUSION

FIELD OF THE INVENTION

This disclosure relates generally to a method and system for detecting a breathing tube occlusion.

BACKGROUND OF THE INVENTION

Medical ventilators are used to provide respiratory support to patients undergoing anesthesia and respiratory treatment whenever the patient's ability to breath is compromised. The primary function of the medical ventilator is to maintain suitable pressure and flow of gases inspired and expired by the patient. The medical ventilator is commonly coupled with a patient via a breathing tube such as, for example, a tracheal tube or an endotracheal tube. The problem is that the breathing tube can become occluded with a mucus plug and/or other debris thereby posing a health risk to the patient and diminishing the effectiveness of the ventilator.

BRIEF DESCRIPTION OF THE INVENTION

The above-mentioned shortcomings, disadvantages and problems are addressed herein which will be understood by reading and understanding the following specification.

In an embodiment, a method for identifying an occlusion in a breathing tube of a ventilator system includes obtaining data related to a respiratory signal, transferring the data to a processor, and implementing the processor to evaluate the data in a manner adapted to automatically identify the presence of an occlusion in the breathing tube.

In another embodiment, a method for identifying an occlusion in a breathing tube of a ventilator system includes providing a sensor, implementing the sensor to measure a respiratory signal, transferring measurement data from the sensor to a processor, implementing the processor to generate a measurement data plot, and implementing the processor to evaluate the measurement data plot in a manner adapted to automatically identify the presence of an occlusion in the breathing tube.

In another embodiment, a ventilator system includes a ventilator, a breathing tube connected to the ventilator, and a sensor connected to either the ventilator or the breathing tube. The sensor is configured to measure a respiratory signal. The ventilator system also includes a processor connected to the sensor. The processor is configured to evaluate data from the sensor in a manner adapted to automatically identify the presence of an occlusion in the breathing tube.

Various other features, objects, and advantages of the invention will be made apparent to those skilled in the art from the accompanying drawings and detailed description thereof.

BRIEF DESCRIPTION OF THE DRAWINGS

FIG. 2a is graph of pressure versus time as measured with both an unobstructed breathing tube and an occluded breathing tube; and FIG. 2b is graph of flow versus time as measured with both an unobstructed breathing tube and an occluded breathing tube.

DETAILED DESCRIPTION OF THE INVENTION

Figure 1:
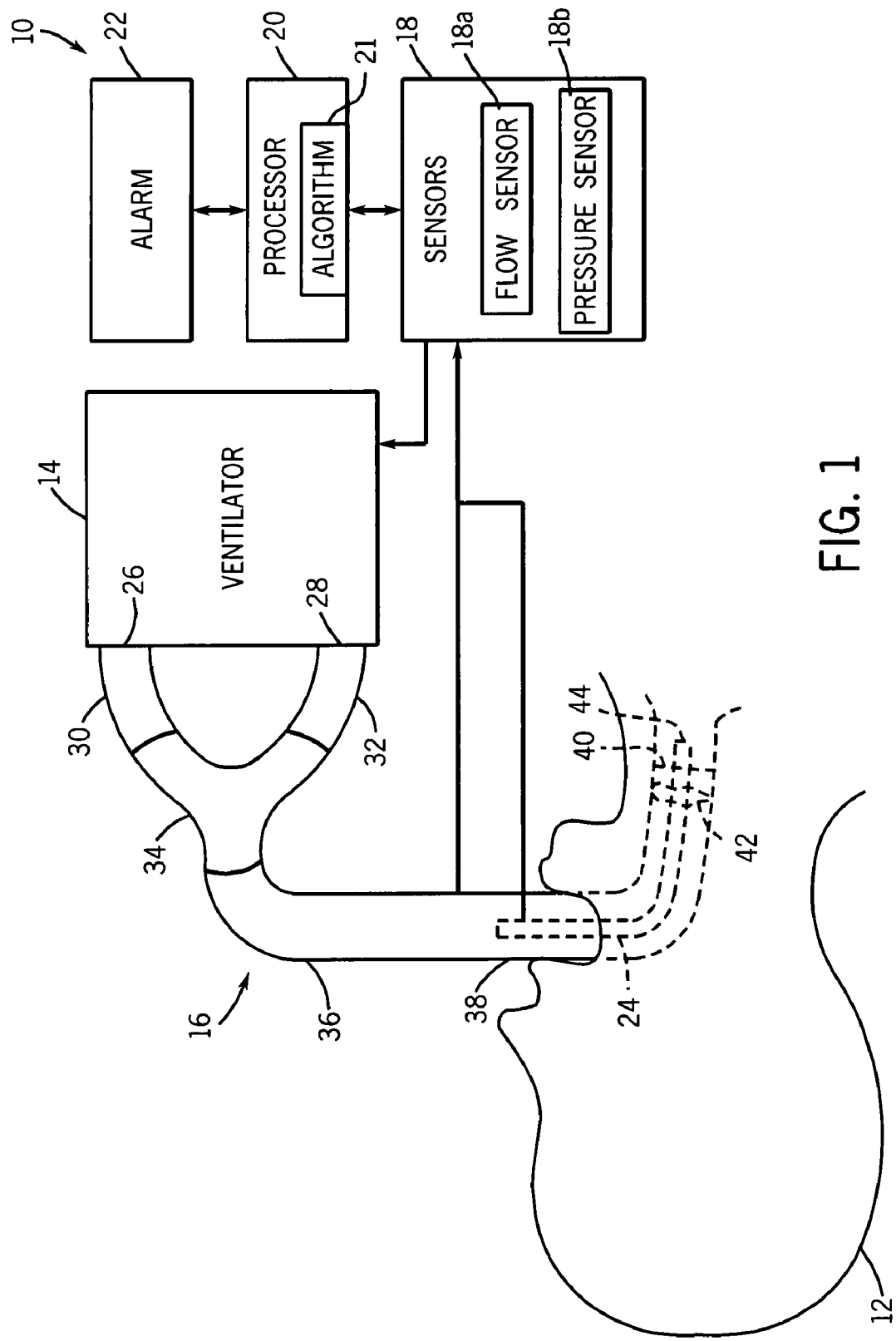
FIG. 1 is a schematic diagram illustrating a ventilator system connected to a patient.

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Referring to FIG. 1, a schematically illustrated ventilator system 10 is shown connected to a patient 12 in accordance with an exemplary embodiment. The ventilator system 10 includes a ventilator 14, a breathing tube or circuit 16, one or more sensors 18, and a processor 20. The ventilator system 10 may also optionally include an alarm 22 and a catheter 24.

The ventilator 14 provides breathing gasses to the patient 12 via the breathing circuit 16. The ventilator 14 includes a plurality of connectors 26, 28 configured to respectively receive an inspiratory branch 30 and an expiratory branch 32 of the breathing circuit 16. The breathing circuit 16 includes the inspiratory branch 30, the expiratory branch 32, a Y-connector 34, a patient branch 36, and an interface 38. The interface 38 is the portion of the breathing circuit 16 that is directly coupled with the patient 12. According to the embodiment depicted and described hereinafter, the interface 38 is an endotracheal tube, however it should be appreciated that other known devices may also be implemented for the interface 38.

The endotracheal tube 38 is generally inserted through the patient's mouth and advanced into the patient's airway until the distal end 40 of the endotracheal tube 38 passes through the patient's larynx (not shown). As is known to those skilled in the art, the endotracheal tube 38 can become occluded or blocked by an occlusion 42 that may, for example, comprise a mucus plug and/or other debris. The occlusion 42 can pose a health risk to the patient 12 and can diminish the effectiveness of the ventilator system 10. As will be described in detail hereinafter, the ventilator system 10 is adapted to automatically identify the presence of an occlusion so that steps may be taken to clear the endotracheal tube 38.

The sensors 18 may be operatively connected to or disposed within the breathing circuit 16 as shown in FIG. 1 and described in detail hereinafter. Alternatively, the sensors 18 may be incorporated into the ventilator 14. The sensors 18 may be configured to monitor respiratory signals such as, for example, flow rate and pressure level, and may therefore include a flow sensor 18a and pressure sensor 18b. The flow sensor 18a and the pressure sensor 18b are known devices and will therefore not be described in detail. According to one embodiment the flow sensor 18a is configured to measure the flow rate of expiratory gasses passing through the breathing circuit 16, and the pressure sensor 18b is configured to measure the pressure within the breathing circuit 16 on the ventilator side of the occlusion 42.

The sensors 18 transmit sensor data to the ventilator 14 and/or the processor 20. As will be described in detail hereinafter, the processor 20 is configured to automatically analyze the sensor data in order to identify an occlusion within the endotracheal tube 38. Advantageously, the automation of this identification process reduces personnel requirements and ensures that the occlusion is identified as quickly as possible. For purposes of this disclosure, "automatic processes" and "automated processes" are those that may be performed independently without direct human interaction. The processor 20 may optionally be connected to an alarm 22 in order to alert hospital personnel to the presence of an occlusion within the endotracheal tube 38.

According to one embodiment, the processor 20 includes an algorithm 21 configured to identify patterns in the sensor data that may be indicative of an occlusion within the endotracheal tube 38. In a non-limiting manner, the following will describe several of these patterns.

Referring to FIG. 2a, an unobstructed pressure plot or graph 50, and an occluded pressure plot or graph 52 are shown. The unobstructed pressure plot 50 represents a pressure versus time plot of a single inhalation/exhalation cycle with an unobstructed endotracheal tube 38 (shown in FIG. 1). Similarly, the occluded pressure plot 52 represents a single inhalation/exhalation cycle with an occluded endotracheal tube 38.

Points 59-66 distinguish the occluded pressure plot 52 from the unobstructed pressure plot 50 and can therefore be implemented to identify the presence of an occlusion within the endotracheal tube 38 (shown in FIG. 1). More precisely, the portions of plot 52 labeled 59, 60, 64 and 65 represent relative minimum points and relative maximum points that are not present in the unobstructed pressure plot 50. Additionally, the portion of the plot 52 labeled 62 is steeper than the corresponding portion of the unobstructed pressure plot 50, and the portion of the plot 52 labeled 66 is less steep than the corresponding portion of the unobstructed pressure plot 50. Therefore, the processor 20 (shown in FIG. 1) may be configured to identify the relative minimum and maximum points 59, 60, 64 and 65, and to evaluate the slope of a pressure plot at or near regions 62 and 66 in order to determine if the endotracheal tube 38 is occluded.

Referring to FIG. 2b, an unobstructed flow plot or graph 70, and an occluded flow plot or graph 72 are shown. The unobstructed flow plot 70 represents a flow versus time plot of a single inhalation/exhalation cycle with an unobstructed endotracheal tube 38 (shown in FIG. 1). Similarly, the occluded flow plot 72 represents a single inhalation/exhalation cycle with an occluded endotracheal tube 38.

Points 73-76 distinguish the occluded flow plot 72 from the unobstructed flow plot 70 and can therefore be implemented to identify the presence of an occlusion within the endotracheal tube 38 (shown in FIG. 1). More precisely, the portions of plot 72 labeled 73, 74, 75 and 76 represent relative minimum points and relative maximum points that are not present in the unobstructed flow plot 70. Therefore, the processor 20 (shown in FIG. 1) may be configured to identify the relative minimum and maximum points 73, 74, 75 and 76 in order to determine if the endotracheal tube 38 is occluded.

Referring again to FIG. 1, the embodiment of the ventilator system 10 wherein the optional catheter 24 is implemented will now be described. The catheter 24 is inserted through the endotracheal tube 38 into the patient's airway such that a distal end 44 of the catheter 24 extends slightly beyond the distal end 40 of the endotracheal tube 38. A pressure sensor 18b may be operatively connected to the catheter 24 in order to obtain a pressure reading at or near the distal end 44 which is on the lung side of the occlusion 42.

Referring to FIG. 2a, an unobstructed pressure plot or graph 80 and an occluded pressure plot or graph 82 measured using the catheter 24 (shown in FIG. 1) are shown with dashed lines. It can be seen that the unobstructed pressure plot 50 measured on the ventilator side of the occlusion 42 (e.g., as measured in the breathing circuit 16) varies only slightly from the unobstructed pressure plot 80 measured on the lung side of the occlusion 42 (e.g., as measured with the catheter 24). Conversely, the occluded pressure plot 52 measured on the ventilator side of the occlusion 42 varies significantly from the occluded pressure plot 82 measured on the lung side of the occlusion 42. Therefore, the processor 20 (shown in FIG. 1) may be configured to compare a pressure measurement taken at a first location (e.g., within the breathing circuit 16) with a pressure measurement taken at a second location (e.g., at or near the distal end 44 of the catheter 24) as an indicator of endotracheal tube 38 occlusion. More precisely, if the processor 20 determines that the pressure measurement taken at the first location varies by more than a predetermined amount from a pressure measurement taken at the second location, the endotracheal tube 38 may be occluded. In addition, sudden increases in the difference between the pressure signals relative the same measurements in previous breaths may trigger an alarm condition.

While the invention has been described with reference to preferred embodiments, those skilled in the art will appreciate that certain substitutions, alterations and omissions may be made to the embodiments without departing from the spirit of the invention. Accordingly, the foregoing description is meant to be exemplary only, and should not limit the scope of the invention as set forth in the following claims.

We claim:

1. A method for identifying an occlusion in a breathing tube of a ventilator system comprising:
   obtaining respiratory data related to the respiration of a patient;
   transferring the respiratory data to a processor; and
   implementing the processor to evaluate the respiratory data to automatically identify the presence of an occlusion in the breathing tube, the evaluation comprising:
   identifying a first data section in the respiratory data that represents an unobstructed respiratory cycle for the patent;
   identifying a second data section in the respiratory data that represents a respiratory cycle for the patient for which the presence of the occlusion in the breathing tube is to be determined;
   calculating a first rate of change of at least a portion of the first data section;
   calculating a second rate of change of at least a portion of the second data section; and
   comparing the second rate of change to the first rate of change to determine if the second rate of change differs from the first rate of change by more than a threshold amount.

2. The method of claim 1, wherein the step of obtaining respiratory data includes implementing one or more pressure sensors or flow sensors to obtain data.

3. The method of claim 1, wherein the step of obtaining respiratory data includes obtaining pressure data.

4. The method of claim 3, wherein the step of implementing the processor to evaluate the respiratory data includes comparing pressure data obtained from a first location in the breathing tube with pressure data obtained from a second location in the breathing tube.

5. The method of claim 1, wherein the step of implementing the processor to evaluate the respiratory data further includes identifying relative minimum values and/or relative maximum values in the second data section and comparing the relative minimum and/or relative maximum values in the second data section to the relative minimum and/or relative maximum values in the first data section.

6. The method of claim 1, wherein the step of obtaining respiratory data includes obtaining flow data.

7. The method of claim 1, further comprising sounding an alarm if the processor identifies the presence of an occlusion in the breathing tube.

8. A method for identifying an occlusion in a breathing tube of a ventilator system comprising:

obtaining flow data related to the respiration of a patient;
transferring the flow data to a processor; and
implementing the processor to evaluate the flow data to automatically identify the presence of an occlusion in the breathing tube, the evaluation comprising:
- identifying a first data section in the flow data that represents an unobstructed respiratory cycle for the patent;
- identifying a second data section in the flow data that represents a respiratory cycle for the patient for which the presence of the occlusion in the breathing tube is to be determined; and
- comparing the second data section to the first data section to determine if the second data section differs from the first data section by more than a threshold amount.

9. The method of claim 8, wherein the step of comparing the first data section to the second data section includes identifying relative minimum values and/or relative maximum values in the second data section and comparing the relative minimum and/or relative maximum values in the second data section to the relative minimum and/or relative maximum values in the first data section.

10. The method of claim 8, wherein the step of implementing the processor to evaluate the flow data further includes comparing the rate of change of the first data section to the rate of change of the second data section.

11. The method of claim 8, further comprising sounding an alarm if the processor identifies the presence of an occlusion in the breathing tube.

12. A method for identifying an occlusion in a breathing tube of a ventilator system comprising:
obtaining pressure data related to the respiration of a patient;
transferring the pressure data to a processor; and
implementing the processor to evaluate the pressure data to automatically identify the presence of an occlusion in the breathing tube, the evaluation comprising:
- identifying a first data section in the pressure data that represents an unobstructed respiratory cycle for the patent;
- plotting the first data section to generate a first pressure versus time plot;
- identifying a second data section in the pressure data that represents a respiratory cycle for the patient for which the presence of an occlusion in the breathing tube is to be determined;
- plotting the second data section to generate a second pressure versus time plot;
- calculating a first slope of at least a portion of the first pressure versus time plot;
- calculating a second slope of at least a portion of the second pressure versus time plot; and
- comparing the second slope to the first slope to determine if the second slope differs from the first slope by more than a threshold amount.

13. The method of claim 8, wherein the step of implementing the processor to evaluate the flow data further includes plotting the first data section to generate a first flow versus time plot and plotting the second data section to generate a second flow versus time plot, and comparing the second flow versus time plot to the first flow versus time plot.

14. The method of claim 12, further comprising sounding an alarm if the processor identifies the presence of an occlusion in the breathing tube.

* * * * *

UNITED STATES PATENT AND TRADEMARK OFFICE
CERTIFICATE OF CORRECTION

| | | |
|---|---|---|
| PATENT NO. | : 7,918,226 B2 | Page 1 of 1 |
| APPLICATION NO. | : 11/733438 | |
| DATED | : April 5, 2011 | |
| INVENTOR(S) | : Acker et al. | |

It is certified that error appears in the above-identified patent and that said Letters Patent is hereby corrected as shown below:

In Column 4, Line 31, in Claim 1, delete "patent;" and insert -- patient; --, therefor.

In Column 5, Line 8, in Claim 8, delete "patent;" and insert -- patient; --, therefor.

In Column 6, Line 7, in Claim 12, delete "patent;" and insert -- patient; --, therefor.

Signed and Sealed this
Second Day of August, 2011

David J. Kappos
*Director of the United States Patent and Trademark Office*